United States Patent
Choi et al.

(10) Patent No.: US 9,303,277 B2
(45) Date of Patent: *Apr. 5, 2016

(54) MICROORGANISMS HAVING IMPROVED ORNITHINE-PRODUCING ABILITY AND METHOD FOR PRODUCING ORNITHINE USING THE SAME

(75) Inventors: Hyang Choi, Anyang-si (KR); Kyoung Min Lee, Daejeon (KR); Min Sun Kang, Yeosu-si (KR); Sung Hoo Jhon, Seoul (KR); Hye Won Um, Suwon-si (KR); Su Jin Choi, Daegu (KR); Han Won Lee, Seoul (KR); Soo An Shin, Seoul (KR)

(73) Assignee: CJ CHEILJEDANG CORPORATION (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/992,241

(22) PCT Filed: Dec. 8, 2011

(86) PCT No.: PCT/KR2011/009477
§ 371 (c)(1),
(2), (4) Date: Jun. 6, 2013

(87) PCT Pub. No.: WO2012/077994
PCT Pub. Date: Jun. 14, 2012

(65) Prior Publication Data
US 2013/0344545 A1    Dec. 26, 2013

(30) Foreign Application Priority Data
Dec. 8, 2010 (KR) .................. 10-2010-0124866
Dec. 7, 2011 (KR) .................. 10-2011-0130594

(51) Int. Cl.
*C12P 13/10* (2006.01)
*C07K 14/34* (2006.01)
*C12N 9/02* (2006.01)
*C12N 9/10* (2006.01)
*C12N 9/12* (2006.01)

(52) U.S. Cl.
CPC ............ *C12P 13/10* (2013.01); *C07K 14/34* (2013.01); *C12N 9/0008* (2013.01); *C12N 9/1018* (2013.01); *C12N 9/1029* (2013.01); *C12N 9/1096* (2013.01); *C12N 9/1217* (2013.01); *C12Y 102/01038* (2013.01); *C12Y 201/03003* (2013.01); *C12Y 203/01035* (2013.01); *C12Y 206/01013* (2013.01); *C12Y 207/02008* (2013.01)

(58) Field of Classification Search
CPC .. C12N 9/0008; C12N 9/1018; C12N 9/1096; C12N 9/1029; C12Y 201/03003; C12Y 206/01013; C12Y 207/02008; C12P 13/10; C07K 14/34

See application file for complete search history.

(56) References Cited

U.S. PATENT DOCUMENTS

2010/0203599 A1 * 8/2010 Lee et al. .................. 435/128

FOREIGN PATENT DOCUMENTS

EP          1801206 A1    6/2007
KR    10-2010-0060909    6/2010

OTHER PUBLICATIONS

GenBank Accession No. CAF19973 "Small-conductance mechanosensitive channel [Corynebacterium glutamicum ATCC 13032]." Nov. 14, 2006.
GenBank Accession No. CAF21409 "Ornithine carbamoyltransferase [Corynebacterium glutamicum ATCC 13032]." Nov. 14, 2006.
Matsui, et al., "Detection of D-ornithine extracellularly produced by Corynebacterium glutamicum ATCC 1302::argF," Bioscience, Biotechnology, and Biochemistry, 74(12):9507-9510, 2010.
Nakamura, et al., "Mutations of the Corynebacterium glutamicum NCgl1221 gene, encoding a mechanosensitive channel homolog, induce L-glutamic acid production," Applied and Environmental Microbiology, 73(14):4491-4498, 2007.
Schneider, et al., "Production of the amino acids l-glutamate, l-lysine, l-ornithine and l-arginine from arabinose by recombinant Corynebacterium glutamicum," Journal of Biotechnology, 154(23):191-198, 2011.
Schneider, et al., "Putrescine production by engineered Corynebacterium glutamicum," Appl Microbiol Biotechnol. 88(4):859-68. Epub 2010.
International Search Report for PCT/KR2011/009477, mailed on Jun. 26, 2012. 3 pages.
Extended European Search Report for EP 11846603.6, mailed on Jun. 3, 2015, 7 pages.
GenBank Accession No. NC_003450, Corynebacterium glutamicum ATCC 13032, complete genome (Apr. 27, 2009).
Hwang, et al., "Effect of increased glutamate availability on L-ornithine production in Corynebacterium glutamicum," J Microbiol Biotechnol. Apr. 2008;18(4):704-10.

* cited by examiner

*Primary Examiner* — Nashaat Nashed
(74) *Attorney, Agent, or Firm* — Cooley LLP

(57) ABSTRACT

The present invention relates to a microorganism having an improved ornithine-producing ability, in which the biosynthetic pathway of arginine form ornithine is blocked, the intracellular glutamate level is increased, and the biosynthetic pathway of ornithine from glutamate is enhanced, and a method for producing ornithine using the microorganism.

8 Claims, 3 Drawing Sheets

MICROORGANISMS HAVING IMPROVED ORNITHINE-PRODUCING ABILITY AND METHOD FOR PRODUCING ORNITHINE USING THE SAME

CROSS-REFERENCES TO RELATED APPLICATIONS

This application is a U.S. national phase application of International PCT Patent Application No. PCT/KR2011/009477, which was filed on Dec. 8, 2011, which claims priority to Korean Patent Application Nos. 10-2011-0130594, filed Dec. 7, 2011 and 10-2010-0124866, filed Dec. 8, 2010. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_022_00US_T25.txt. The text file is 39 KB, was created on, Aug. 28, 2013, and is being submitted electronically via EFS-Web.

TECHNICAL FIELD

The present invention relates to a microorganism having an improved ornithine-producing ability, and a method for producing ornithine using the same.

BACKGROUND ART

Ornithine is a substance widely found in plants, animals, and microorganisms and is used as a precursor in the biosynthesis of arginine, proline, and polyamines. As a non-essential amino acid, ornithine is not found in proteins, but is present in peptide antibiotics such as tyrosidine and gramicidine. Ornithine plays an important role in the pathway for excretion of urea produced from amino acid or ammonia via the ornithine cycle in the in vivo metabolism of higher animals.

Ornithine helps to build muscles and to reduce body fat, and thus is used as a nutritional supplement. Ornithine-alpha ketoglutarate (OKG) containing ornithine and alpha ketoglutaric acid at a ration of 2:1 is used as an immune enhancer. Ornithine is also used a drugs for improving liver cirrhosis and liver function disorders, because it helps to remove harmful ammonia from the liver. The known methods of producing ornithine are treatment of milk casein with digestive enzymes and use of transformed E. coli or industrial microorganisms belonging to Corynebacterium sp., which are widely used in the production of amino acids, nucleic acids, enzymes and antibiotic-like substances.

In the microorganisms belonging to Corynebacterium sp., L-arginine is synthesized from glutamate by an enzyme expressed from a gene on the arginine operon in the form of argCJBDFRGH. The arginine operon genes, which play the most important role in arginine biosynthesis, synthesize arginine using intracellular glutamate (L-glutamate) as a substrate, and ornithine is produced as an intermediate during the syntheses of arginine. Specifically, as in FIG. 2 schematically illustrating a synthetic pathway of arginine from glutamate in a microorganism belonging to Corynebacterium sp., it is known that argJ encodes an enzyme converting glutamate to N-acetyl glutamate, argB encodes an enzyme converting N-acetyl glutamate to N-acetylglutamyl phosphate, argC encodes an enzyme converting N-acetylglutamyl phosphate to N-acetyl glutamate semialdehyde, argD encodes an enzyme converting N-acetyl glutamate semialdehyde to N-acetyl ornithine, argJ encodes an enzyme converting N-acetyl ornithine to ornithine, argF encodes an enzyme converting ornithine to citrulline, argG encodes an enzyme converting citrulline to argininosuccinate, and argH encodes an enzyme converting argininosuccinate to arginine in the arginine synthetic pathway, and the ornithine synthetic pathway is included in the arginine synthetic pathway.

The known arginine-producing strains have been developed by introducing a mutation into the arginine operon or by promoter mutation to increase the expression levels of the enzymes involved in the arginine biosynthesis. Of them, argR controlling and suppressing the arginine operon expression and argB inhibited by arginine level have been widely studied as targets for increasing arginine production (Korean Patent Publication No. 2010-0060909)

To improve ornithine productivity, it is known that ornithine production is increased by the action of ornithine cyclodeaminase (ocd) by culturing the Corynebacterium microorganism in a medium supplemented with proline, or by modifying impellers and culturing conditions during the culture of the microorganism. Also, when a transformed E. coli is used, ornithine productivity is improved by culturing argF and argR-deleted strains in a medium supplemented with glutamate, or by using a transformed strain with the deletion of proB gene encoding γ-glutamulkinase involved in the first step of the synthetic pathway of proline from glutamate rather that the synthetic pathway of ornithine form glutamate.

Furthermore, Corynebacterium glutamicum have been consistently studied for the high-yield production of glutamate as an ornithine precursor. Glutamate excretion from Corynebacterium glutamicum is known to be increased by biotin limitation of treatment with penicillin G or a fatty acid ester surfactant. Since these treatments are correlated with damage in the cell wall, it had previously been thought that glutamate leaks passively through the damaged cell wall.

NCgl1221 protein derived from the wild type Corynebacterium glutamicum (Cgl 13032) facilities betaine efflux, and its amino acid sequence is similar to that of the E. coli mechanosensitive channel protein, yggB (Korean Patent Publication No. 2010-0017581).

DISCLOSURE

Technical Problem

In this background, the present inventors have made many efforts to develop a strain capable of producing the useful ornithine in a higher yield. As a result, they found that an ornithine-overproducing strain can be developed by blocking the biosynthetic pathway of arginine from ornithine, by blocking a protein involved in glutamate export to increase the intracellular glutamate level and by enhancing the biosynthetic pathway of ornithine from glutamate, thereby completing the present invention.

Technical Solution

An object of the present invention is to provide a microorganism having an improved ornithine-producing ability. Another object of the present invention is to provide a method for producing ornithine using the microorganism.

Advantageous Effect

The microorganism of the present invention having an improved ornithine-producing ability can be more effectively used in a wide variety of applications for ornithine production.

BEST MODE

Figure 1:
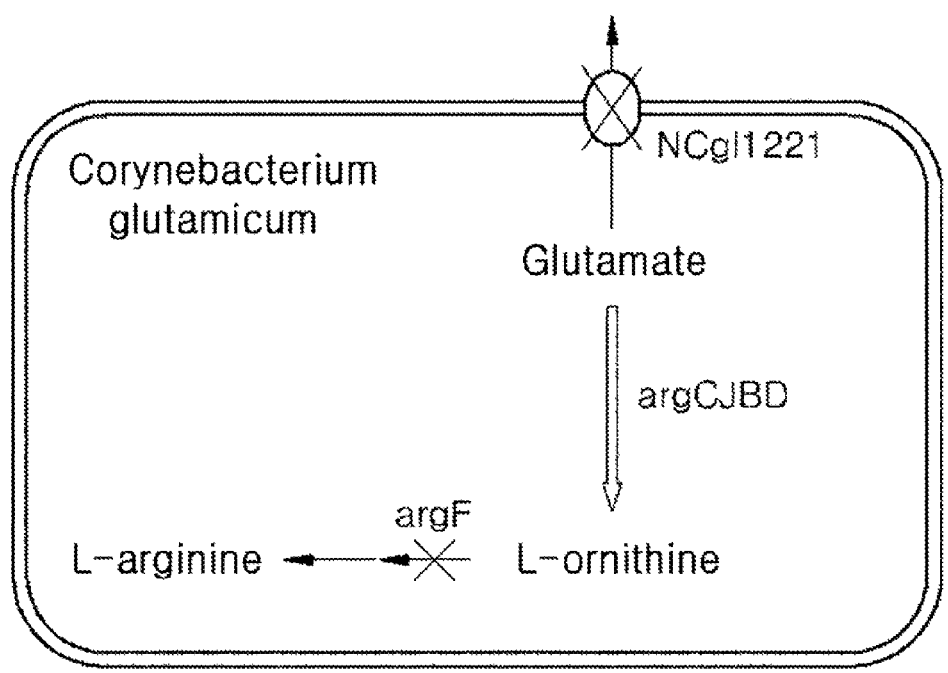
FIG. 1 shows the ornithine biosynthetic pathway and related genes of the transformed *Corynebacterium glutamicum* of the present invention.
Figure 2:
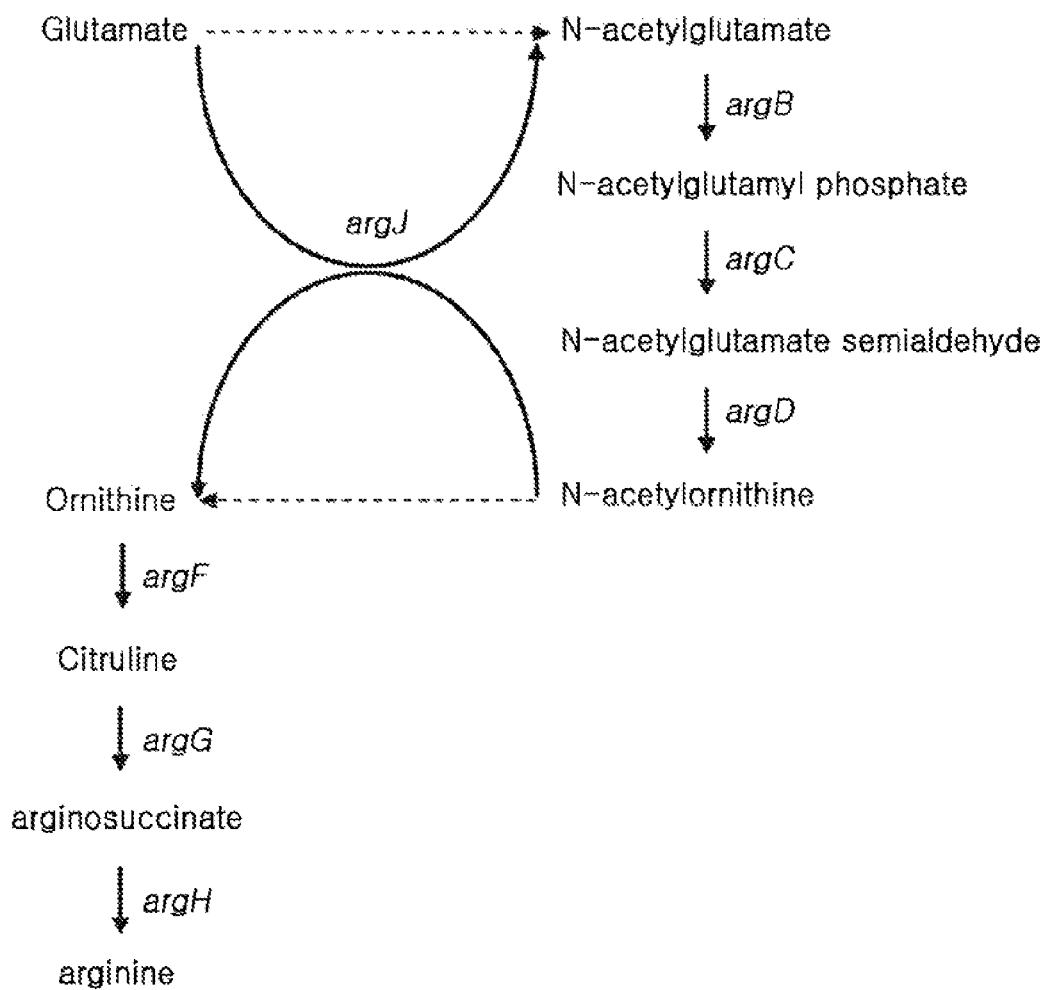
FIG. 2 shows the known arginine biosynthetic pathway of the *Corynebacterium glutamicum*.

In one aspect to achieve the above objects of the present invention, the present invention provides a microorganism having an improved ornithine-producing ability, in which the activities of ornithine carbamoyltransferase and a protein involved in glutamate export (NCgl1221) are modified to be attenuated, compared to their endogenous activities.

As used herein, "ornithine carbamoyltranferase (OCT)" refers to a catalytic enzyme that mediates the reaction between carbamoyl phosphate and ornithine to synthesize citrulline and phosphoric acid. OCT is present in a liver of urea-excreting animals as well as plant and microorganism, and in microorganism it is involved in arginine synthesis. The OCT enzyme comprises catalytic domain and regulatory domain, and when ornithine binds to the regulatory domain the enzyme activity is inhibited.

*E. coli* K12 strain has two types of OCT (ArgF and ArgI), and intestinal microorganism including *E. coli* B and W strains have OCT protein similar to ArgI. OCTs encoded by argF and argI have different amino acid sequences from each other, but they are considered as isoenzyme having the same function (EMBO J. (1982) 1:853857). *Corynebacterium* sp. strain only has OCT encoded by argF gene. OCT only acts in the synthetic pathway from ornithine to arginine, and thus if the OCT activity is weakened, the intracellular ornithine level can be increased.

For accumulation intracellular ornithine, the present invention provides a *Corynebacterium* microorganism in which the synthetic pathway of arginine from ornithine is blocked To achieve this, a transformed strain with a deletion of ornithine carbamoyltransferase-encoding gene was prepared. In this regard, the. ornithine carbamoyltransferase may be, but is not particularly limited to, a protein having an amino acid sequence of SEQ ID NO. 18, or a protein having 70% or more homology with the sequence, more preferably 80% or more homology with the sequence, much more preferably 90% or more homology with the sequence.

As used herein, "homology" refers to the similarity in nucleotide sequences or amino acid sequences of gene coding for a protein. When homology is sufficiently high, products of the corresponding gene may be the same or have a similar activity.

As used herein, "protein involved in glutamate export" refers to a type of mechanosensitive channels which function to export the intracellularly produced glutamate to extracellular environment. The present invention provides a *Corynebacterium* microorganism having improved ornithine productivity. For this work, a transformed strain capable of maintaining a high level of intracellular glutamate is prepared by deleting a gene encoding the protein that functions to excrete glutamate which is a raw material for ornithine synthesis.

By increasing the intracellular level of glutamate, i.e., a precursor of ornithine, an ornithine biosynthetic pathway can be stimulated. In the present invention, glutamate exporting can be reduced or inhibited by diminishing the NCgl1221 activity.

The removed protein involved in glutamate export may be a protein having an amino acid sequence of SEQ ID No. 20 or an amino acid sequence having 70% or more homology thereto, and more preferably having 80% or more homology, even more preferably having 90% or more homology thereto, but is not limited thereto.

The activity of the ornithine carbamoyltransferase and the protein involved in glutamate export can be diminished by a method selected from the group consisting of (1) a partial or full deletion of a gene coding for the protein, (2) modification of an expression regulatory sequence for suppressing the gene expression, (3) modification of the nucleotide sequence on chromosome for diminishing the protein activity, and 4) a combination thereof, but is not limited thereto.

A partial or full deletion of a polynucleotide coding for the protein can be done by introducing a vector for chromosomal insertion into a microorganism, thereby replacing the polynucleotide coding for an endogenous target protein on chromosome with a partially removed polynucleotide or a marker gene. The length "partial" may vary depending on the type of polynucleotide, but specifically it refers to a length of 1 to 300 nucleotides, preferably 1 to 100 nucleotides, and more preferably 1 to 50 nucleotides.

Also, modification of an expression regulatory sequence for reducing expression of the polynucleotide can be done by inducing a modification on the expression regulatory sequence through deletion, insertion, non-conservative or conservative substitution of nucleotide sequence, or a combination thereof in order to diminish the activity of expression regulatory sequence, or by replacing the expression regulatory sequence with a nucleotide sequence having weaker activity. The expression regulatory sequence includes a promoter, an operator sequence, a sequence coding for ribosome-binding site, and a sequence regulating the termination of transcription and translation.

Furthermore modification of a polynucleotide sequence on chromosome, which codes for the enzyme of the present invention, can be done by inducing a mutation on the sequence through deletion, insertion, non-conservative or conservative substitution of polynucleotide sequence, or a combination thereof in order to diminish the enzymatic activity, or by replacing the sequence with a polynucleotide sequence which is modified to have weaker activity.

An used herein, "endogenous activity" refers to the activity of enzyme that a microorganism possesses in its native state. In the present invention, endogenous activity refers to the activity of ornithine carbamoyl transferase and a protein involved in glutamate export, i.e., NCgl1221 that a microorganism naturally possesses. Also, as used herein, "modified to have a weaker activity than an endogenous activity" refers to the state where an ornithine carbamoyl transferase and a protein involved in glutamate export, i.e., NCgl1221 do not function properly due to gene deletion or mutation and thus the activity of ornithine carbamoyl transferase and a protein involved in glutamate export, i.e., NCgl1221 that microorganism naturally possesses is weakened.

As used herein, the term "microorganism having an improved ornithine-producing ability" refers to a microorganism having a higher ornithine-producing ability than the parent strain, and the microorganism having an improved ornithine-producing ability may be, but is not particularly limited to, a microorganism that is further transformed to have higher activity acetylglutamate synthase (ArgJ) converting glutamate to acetyl glutamate (N-acetyl glutamate) or ornithine acetyltransferase (ArgJ) converting acetyl ornithine to ornithine, acetylglutamate kinase (ArgB) converting acetyl glutamate to acetylglutamyl phosphate (N-acetylglutamyl phosphate), acetyl gamma glutamyl phosphate reductase (ArgC) converting acetyl glutamyl phosphate to acetyl glutamate semialdehyde (N-acetyl glutamate semialdehyde), acetylornithine aminotransferase (ArgD) converting acetyl glutamate semialdehyde to acetylornithine (N-acetylornithine) or the like than the endogenous activity, in order to enhance the biosynthetic pathway of ornithine from glutamate.

The transformed microorganism was prepared by a method different from the known method of developing an ornithine-producing strain, that is, the known method is performed by eliminating or attenuating the function of ArgG that acts as a transcriptional inhibitor in the arginine biosynthetic pathway to increase ornithine production and by further deleting the ornithine carbamoyltransferase gene and introducing feedback-resistant N-acetylglutamate synthase to increase ornithine production (Korean Publication No. 2010-0060909).

In this regard, the acetyl gamma phosphate reductase (ArgC), acetylglutamate synthase or ornithine acetyltransferase (ArgJ), acetylglutamate kinase (ArgB), and acetylornithine aminotransferase (ArgD) may preferably have, but is not particularly limited to, the amino acid sequences of SEQ ID NOs. 23, 25, 27, and 29, or 70% or more homology with the sequence, more preferably 80% or more homology with the sequence, and much more preferably 90% or more homology with the sequence, respectively. The increase in their activity may be performed by any one or more methods selected from the group consisting of 1) an increase in the copy number of a polynucleotide encoding the protein, and 2) an increase in the polynucleotide expression by modification of the expression control sequence, 3) enhancement of the enzyme activity by modification of the polynucleotide sequence on the chromosome, and 4) enhancement by a combination thereof.

To be specific, various methods can be used to increase the enzymatic in a microorganism in general. For example, the expression level of a polynucleotide can be increased by increasing the copy number of the polynucleotide transformation involving plasmid insertion, homologous recombination, conjugation, and translocation; modifying an expression regulatory sequence of the polynucleotide; amplifying a gene coding for a regulatory factor which stimulates the polynucleotide expression; or by deleting or inhibiting a gene coding for a regulatory factor which suppresses the polynucleotide expression. To be more specific, the expression level of a polynucleotide can be increased by operably linking a gene fragment comprising the polynucleotide to a multicopy vector which can be replicated in *Corynebacterium* sp. strains, by introducing single of multiple copies of the polynucleotide to the chromosome, or by replacing the expression regulatory sequence of polynucleotide with one having an improved activity including a strong promoter.

Figure 3:
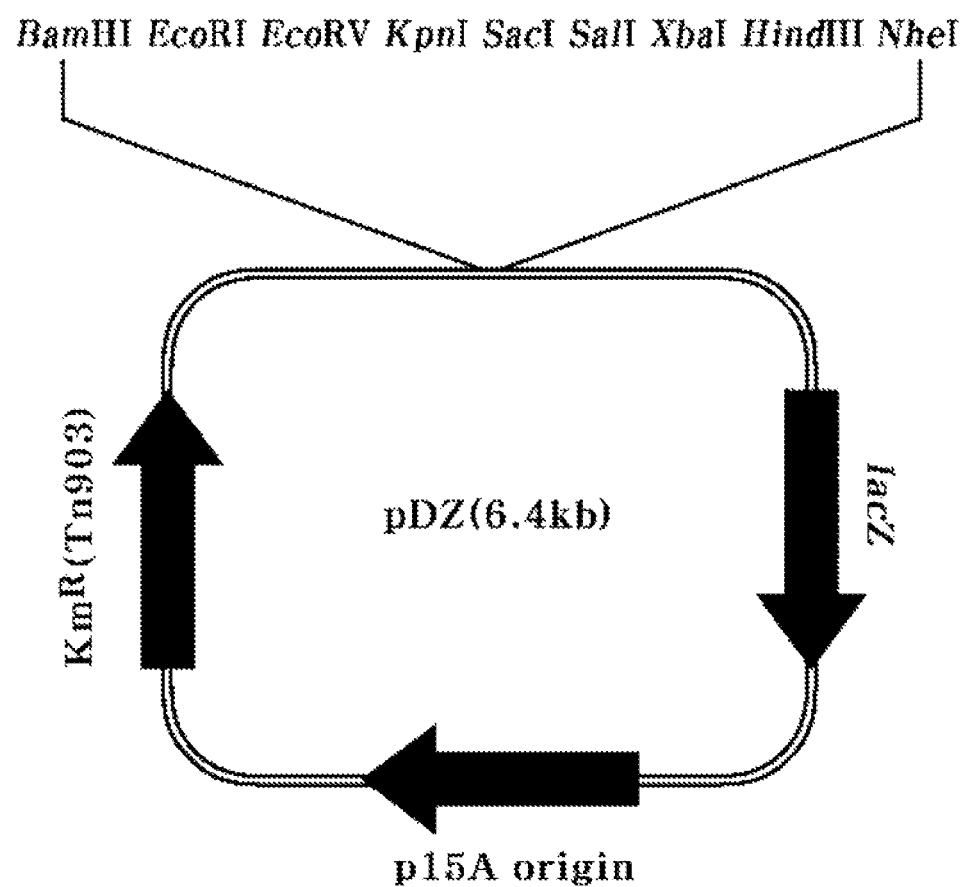
FIG. 3 shows a pDZ vector to be inserted into chromosome of the microorganism belonging to the *Corynebacterium* sp.

For instance, the argCJBD gene group may be transformed into a microorganism by using pHC139T vector to prepare a microorganism with significantly improved ornithine productivity. Alternatively, a microorganism in which ornithine biosynthetic pathway is enhanced may be prepared by improving a promoter region regulating the expression of argCJBD gene in the chromosome of microorganism or by replacing a promoter region by a promoter with more improved activity. In particular, a method for improving promoter region may involve, for replacing a promoter within the chromosome, preparing a gene fragment comprising nucleotide sequences of both terminal sites adjacent to the target site on the chromosome and a promoter sequence to be inserted in the same form as in the chromosome and following the same gene deletion method using a pDZ vector published by Korea Patent Publication No. 2009-0082702, but is not limited thereto. Here, the improved promoter may preferably be, but is not limited to, the pcj7 (or P(CJ7) promoter having a nucleotide sequence of SEQ ID No. 30 (Korea Patent Registration No. 0620092). The pDZ vector may preferably be, but is not limited to, a vector represented by a cleavage map of FIG. 3.

As used herein, "vector" reek to a DNA construct comprising a nucleotide sequence of gene which is operably linked to so appropriate expression regulatory sequence to express a target gene in a suitable host cell. The expression regulatory sequence comprises a promoter that can initiate transcription, an optional operator sequence for regulating the transcription, a sequence coding for a suitable mRNA ribosome binding site, and a sequence regulating the termination of transcription and translation.

Examples of conventional vectors include a natural or recombinant plasmid, cosmid virus and bacteriophage. For instance, pWE15, M13, λEMBL3, λEMBL4, λFIXII, λDASHII, λZAPII, λgt11, λgt11, Charon4A, and Charon21A can be used as a phage vector or cosmid vector. As a plasmid vector, pDZ vector, pBR type, pUC type, pBluescriptII type, pGEM type, pTZ type, pCL type, and pET type may be used. A usable vector is not particularly limited, and any known expression vector preferably pDZ vector, can be used.

Meanwhile, the microorganism of the present invention may be, but is not particularly limited to, a microorganism prepared by transformation of a microorganism belonging to the *Escherichia* sp., the *Shigella* sp., the *Citrobacter* sp., the *Salmonella* sp., the *Enterobacter* sp., the *Yersinia* sp., the *Klebsiella* sp., the *Erwinia* sp., the *Corynebacterium* sp., the *Brevibacterium* sp., the *Lactobacillus* sp., the *Selenomanas* sp., or the *Vibrio* sp., which has the activities of ornithine carbamoyltransferase and a protein involved in glutamate export (NCgl1221).

Preferably, the microorganism of the present invention may be may be *Corynebacterium* sp. strain, and more preferably *Corynebacterium glutamicum*. To be more specific, a wild-type strain *Corynebacterium glutamicum* ATTC 13032 f or a glutamate-overproducing strain KCCM-10735P (Korea Patent Publication No. 2008-0034334) may be used, but is not limited thereto. The KCCM-10785p strain is a glutamate-overproducing strain generated by deleting cg2624 (NCBI LOCUS ID YP_226636) and cg2115 (NCBI LOCUS ID YP_11074) which was generated by using mutagen such as N-methyl-N'-nitro-N-nitrosoguanidine (NTG). Although glutamate overproduction by deletion of cg2624 and cg2115 have not been identified prior to the above publication, cg2624 is identified as pcaR, which is an IclR family regulatory protein, and the cg2115 is identified as sugR, which is a transcriptional regulator of sugar metabolism.

According to one embodiment of the present invention, a *Corynebacterium glutamicum* strain with a deletion of argF gene (ATTC 13032 ΔarF and KCCM-10785P ΔargF) (Example 1), a *Corynebacterium glutamicum* strain with deletions of argF and NCgl1221 genes (ATCC 13032 ΔargF ΔNCgl1221 and KCCM-10785P ΔargF ΔNCgl1221) (Example 2), a *Corynebacterium glutamicum* strain with deletions of argF and NCgl1221 genes and with an introduction of argCJBD gene (ATCC 13032 ΔargF ΔNCgl1221/pHC139T-argCJBD (Cgl) and KCCM-10785P ΔargF ΔNCgl1221/pHC139T-argCJBD (Cgl)) (Example 3-1), and a *Corynebacterium glutamicum* strain with deletions of argF and NCgl1221 genes and with replacement of the promoter of the argCJBD gene cluster in the chromosome (ATCC 13032 ΔargF ΔNCgl1221 P(CJ7)-argCJBD and KCCM-10785P ΔargF ΔNCgl1221 P(CJ7)-argCJBD) (Example 3-2) were prepared. The result of comparing their ornithine productivities showed that the *Corynebacterium glutamicum* strain with deletions of argF and NCgl1221 genes and with replacement of the promoter of the argCJBD gene cluster in the chromosome (ATCC 13032 ΔargF ΔNCgl1221 P(CJ7)-argCJBD and KCCM-10785P ΔargF ΔNCgl1221 P(CJ7)-argCJBD) has excellent ornithine productivity (Tables 5 and 6).

Therefore, the ornithine-producing strain having an improved ornithine-producing ability was designated as "CC01-0061 (ATCC 13032 ΔargF ΔNCgl1221 P(CJ7)-argCJBD)", and deposited under the Budapest Treaty to the Korean Culture Center of Microorganisms whose address is Hongje-1-dong, Seodaemun-gu, Seoul on Nov. 24, 2010, with Accession No. KCCM11137P.

In another aspect of the present invention to achieve the above objects, the present invention provides a method for producing ornithine, including the steps of (i) culturing the microorganism having an improved ornithine-producing ability to obtain a culture; and (ii) recovering ornithine from the cultured microorganism or the culture.

In the method, culturing the microorganism may preferably be done by batch culture, continuous culture, and fed-batch culture known in the art, but is not limited thereto. Furthermore, as for the culturing condition, and optimal pH of 5 to 9, preferably pH 6 to 8, and most preferably pH6.8 can be maintained by using a basic chemical (for example: sodium hydroxide, potassium hydroxide or ammonia) or acidic chemical (for example: phosphoric acid or sulfuric acid). Also, an aerobic condition can be maintained by adding oxygen or oxygen-containing gas mixture to a cell culture. The culturing temperature may be maintained at 20° C. to 45° C., and preferably at 25° C. to 40° C. In addition, it is preferable to culture for about 10 to 160 hours. The ornithine produced by the above culturing may be excreted to a culture medium or remain inside the cell.

Furthermore, the medium for culturing may comprise sugar and carbohydrate (for example: glucose, sucrose, lactose, fructose, maltose, molasse, starch and cellulose), oil and fat (for example: soybean oil, sunflower seed oil, peanut oil and coconut oil), fatty acid (for example: palmitic acid, stearic acid and linoleic acid), alcohol (for example: glycerol and ethanol), and organic acid (for example: acetic acid) individually or in combination as a carbon source; nitrogen-containing organic compound (for example: peptone, yeast extract, meat juice, malt extract, corn solution, soybean meal powder and urea), or inorganic compound (for example: ammonium sulfate, ammonium chloride, phosphate or ammonium, ammonium carbonate, and ammonium nitrate) individually or in combination as a nitrogen source; potassium dihydrogen phosphate, dipotassium phosphate, or sodium-containing salt corresponding thereto individually or in combination as a phosphorus source; other essential growth-stimulating substances including metal salts (for example: magnesium sulfate or iron sulfate), amino acids, and vitamins.

[Mode for Invention]

Hereinafter, the present invention will be described in more detail with reference to Examples. However, these Examples are for illustrative purposes only, and the invention is not intended to be limited by these Examples.

EXAMPLE 1

Preparation of argF-Deleted *Corynebacterium Glutamicum* Strain

In this example, and argF-deleted strain was prepared from a wild-type *Corynebacterium glutamicum* strain ATCC 13032 and a glutamate-overproducing strain KCCM-10785P which was generated by deleting cg2624 and cg2115 genes in a glutamate-producing strain KFCC-11074 generated by using mutagen such as NTG (Korea Patent Publication No. 2008-0034334) in order to block a synthetic pathway or arginine from ornithine. The arginine biosynthetic genes of *Corynebacterium glutamicum* ATCC 13032 are organized in an operon having a form of argCJBDFRGH, and a deletion target argF gene (SEQ ID No. 17) is present adjacent to the genes coding for enzymes involved in ornithine synthetic pathway on the chromosome. Thus, a plasmid for deleting argF gene was prepared based on the nucleotide sequence of argD and argR which are located adjacent to the deletion target argF gene.

To be specific, based on the nucleotide sequence of argD and argR of the ATCC 13032 strain, a homologous recombination fragment adjacent to the N-terminal sequence of argF and a homologous recombination fragment adjacent to the C-terminal sequence of argF were constructed. For this, the fragment adjacent to the N-terminal sequence of argF was obtained by PCR using the genomic DNA from ATCC 13032 strain as a template, and primers (SEQ ID Nos. 1 and 2) (28 cycle of denaturation for 30 seconds at 94° C., annealing for 30 seconds at 55° C., and extension for 30 seconds at 72° C.). Likewise, the fragment adjacent to the C-terminal sequence of argF was obtained by PCR using the genomic DNA from ATCC 13032 strain as a template, and primers (SEQ ID Nos. 3 and 4) under same PCR condition (Table1)

TABLE 1

Primers for preparation of argF-deleted strain (ΔargF)

| Name | SEQ. ID NO. | Sequence(5'-3') |
|---|---|---|
| argF-del-F1_BamHI | 1 | CGGGATCCTGGCCGTACCGGCGATTTCT |
| argF-del-R1_SalI | 2 | CGCGTCGACAAGTTTGAGTCCTTTATGCG |
| argF-del-F2_SalI | 3 | CGCGTCGACGACATGTCCCTTGGCTCAAC |
| argE-del-R2_XbaI | 4 | TGCTCTAGAAGTAATTCACCTAGTTCTTTACC |

The above-prepared homologous recombination fragment adjacent to the N-terminal sequence of argF was digested with BamHI and SalI, and the homologous recombination fragment adjacent to the C-terminal sequence of argF was digested with SalI and XbaI. Then each of the cleaved fragments were inserted into the pDZ vector which was also digested with BamHI and XbaI, thereby producing a plasmid pDZ-argF(K/O).

The above-prepared plasmid pDZ-argF(K/O) was transformed into the ATCC 13032 strain and KCCM-10785P strain. Then, the transformed strains were plated and cultured on BHIS plate Braine heart infusion 37 g/l, sorbitol 91 g/l, agar 2%) which contains kanamycin (25 µg/ml) and X-gal (5-bromo-4-chloro-3-indolin-β-D-galactoside), while letting the colonies to grow on the plate. Among the colonies formed on the plate, colonies with blue colour was collected to select for the strain inserted with the plasmid pDZ-argF(K/O).

The above-selected strains were cultured with shaking in CM medium (glucose 10 g/l, polypeptone 10 g/l, yeast extract 5 g/l, beef extract 5 g/l, NaCl 2.5 g/l, urea 2 g/l, pH 6.8) at 30° C. for 8 hours. Subsequently, each cell culture was serially diluted from $10^{-4}$ to $10^{-10}$. Then the diluted samples were plated and cultured on an X-gal-containing solid medium letting the colonies to grow. Among the colonies formed on the plate, only the white colonies which appear at relatively low frequency were collected to select for the argF-deleted strains.

Successful insertion of the plasmid pDZargF(K/O) into the above-selected strains was confirmed by performing PCR using the chromosomal DNA from the above-selected strain as a template, and primers of SEQ ID Nos. 1 and 4. Through this PCR confirmation, it was confirmed that the above-selected strain is the argF-deleted strain (i.e., ATCC 13032 ΔargF and KCCM-10785P ΔargF).

EXAMPLE 2

Preparation of argF- and NCgl1221-deleted *Corynebacterium Glutamicum* Strain

NCgl1221 gene encoding the protein involved in glutamate export was further deleted in ATCC 13032 ΔargF strain and KCCM-10785P ΔargF strain obtained in Example 1 in order to increase the intracellular of glutamate which is an ornithine precursor.

To be specific, based on the nucleotide sequence (SEQ ID No. 19) of NCgl1221 the ATCC 13032 strain, a homologous recombination fragment adjacent to the N-terminal sequence of NCgl1221 and a homologous recombination fragment adjacent to the C-terminal sequence of NCgl1221 were constructed. For this, the fragment adjacent to the N-terminal adjacent sequence of NCgl1221 was generated by PCR using the genomic DNA from ATCC13032 strain as a template and primers (SEQ ID Nos. 5 and 6), and the fragment adjacent to the C-terminal sequence of NCgl1221 was generated by PCR using the genomic DNA from ATCC 13032 strain as a template and primers (SEQ ID Nos. 7 and 8) under the same PCR condition as in Example 1 (Table 2).

TABLE 2

Primers for preparation of NCgl1221-deleted strain

| Name | SEQ ID NO. | Sequence (5'-3') |
|---|---|---|
| NCgl1221-del-F1_BamHI | 5 | CGGGATCCGTCCAAGCCAAGCCGATTTCAAC |
| NCgl1221-del-R1_SalI | 6 | ACGCGTCGACCCACTCGGCGCTTGATAATAC |
| NCgl1221-del-F2_SalI | 7 | ACGCGTCGACCTGGAACAAGAACTCTCCAGC |
| NCgl1221-del-R2_XbaI | 8 | CTAGTCTAGA GGTTGGTGCTTCCACTGCTG |

The above-prepared homologous recombination fragment adjacent to the N-terminal sequence of NCgl1221 was digested with BamHI and SalI. Likewise, the homologous recombination fragment adjacent to the C-terminal sequence of NCgl1221 was digested with SalI and XbaI. Then each of the cleaved fragments was inserted into the pDZ vector that was cleaved with BamHI and XbaI, thereby producing a plasmid pDZ-NCgl1221(K/O).

The above-prepared plasmid pDZ-NCgl1221(K/O) was transformed into ATCC 13032 ΔargF strain and KCCM-10785P ΔargF strain. Then, the transformed strains were plated and cultured on BHIS plate (Braine heart infusion 37 g/l, sorbitol 91 g/l, agar 2%) which contains kanamycin (25 µg/ml) and X-gal (5-bromo -4-chloro-3-indolin-β-D-galactoside), while letting the colonies to grow on the plate. Among the colonies formed on the plate, colonies with blue colour was collected to select for the strain inserted with the plasmid pDZ-NCgl1221(K/O).

The above-selected strains were cultured with shaking in CM medium at 30° C. for 8 hours. Subsequently, each cell culture was serially diluted from $10^{-}$ to $10^{-10}$. then the diluted samples were plated and cultured on an X-gal-containing solid medium, letting the colonies to grow. Among the colonies formed on the plate, only the white colonies which appear relatively low frequency were collected to select for the NCgl1122l-deleted strains.

Successful insertion of the plasmid pDZ-NCgl1221(K/O) into the above-selected strains was confirmed by performing PCR using the chromosomal DNA from the above-selected strain as a template, and primers of SEQ ID Nos. 5 and 8. The selected NCgl1221-deleted strains were named as ATCC 13032 ΔargF ΔNCgl1221 or KCCM-10785P ΔargF ΔNCgl1221 accordingly.

EXAMPLE 3

Preparation of argCJBD-introduced *Corynebacterium Glutamate* Strain

EXAMPLE 3-1

Cloning of argCJBD Gene and Preparation of Transformant

In this example, a vector inserted with argC, argJ, argB, and argD genes (SEQ ID Nos. 22, 24, 26, and 28 and respectively) was prepared and a transformant was prepared by introducing the same, in order to enhance the ornithine synthetic pathway by increasing the copy number of argCJBD (SEQ ID No. 21, comprising the promoter region) which codes for the enzymes involved in a synthetic pathway of ornithine from glutamate.

First, PCR was performed to obtain argCJBD gene by the chromosome of ATCC 13032 strain as a template and primers (SEQ ID Nos. 9 and 10, Table 3) (30 cycles of denaturation for 40 seconds at 95° C., annealing for 40 seconds at 55° C., and extension for 150 seconds at 72° C.), thereby obtaining a gene fragment having a size of 4,900 bp.

TABLE 3

Primiers for acquisition of argCJBD gene fragment of ATCC 13032

| Name | SEQ ID NO. | Sequence (5'-3') |
|---|---|---|
| P_argC-5-KpnI | 9 | CGGGGTACCCTCCTCCAGCAGCTCTAGCTC |
| argD-3_XbaI | 10 | TGCTCTAGAAAGTTTGAGTCCTTTATGCG |

The above-prepared gene fragment was run through gel electrophoresis on 0.8% agarose gel, and a band of the target size was cut and DNA sample was isolated therefrom. The isolated DNA was digested with KpnI and XbaI to obtain a fragment, then the cleaved fragment was cloned into a pHC139t-gfp vector (Korea Patent Publication No. 2008-0074286), thereby producing an expression vector pHC139T-argCJBD(Cgl).

Subsequently, the expression vector pHC139T-argCJBD (Cgl) prepared for increasing the production level of ornithine in the cell was introduced into ATCC 13032 ΔargF NCgl1221 strain and KCCM-10785P and ΔargF ΔNCgl1221 strain through electroporation. Then, a successful transformant was selected by plating the transformed cells on BHIS plate containing 25 μg/ml kanamycin. Finally, each of the selected transformants was named as ATCC 13032 ΔargF ΔNCgl1221/pHC139T-argCJBF(Cgl) and KCCM-10785P ΔargF ΔNCgl1221/pHC139T-argCJBD(Cgl) accordingly.

EXAMPLE 3-2

Substitution of the Promoter of argeCJBD Gene in the Chromosome

In this example, a promoter of argCJBD was substituted with CJ7 promoter which was newly developed by the present applicant in the chromosome, in order to increase the expression level by removing the regulation of the argCJBD gene which codes for the enzymes involved in a synthetic pathway ornithine from glutamate.

First, a homologous recombination fragment comprising a CJ7 promoter and a nucleotide sequence of both terminal sites of the promoter was prepared.

To be specific, the nucleotide sequence of 5'-terminal site of CJ7 promoter was obtained by performing PCR using the genomic DNA from ATTC 13032 strain as a template and primers (SEQ ID Nos. 11 and 12) (28 cycles of denaturation for 30 seconds at 94° C., annealing for 30 seconds at 55° C., and extension for 30 seconds at 72° C.). Likewise, the nucleotide sequence of CJ7 promoter region was obtained by PCR using primers (SEQ ID Nos. 13 and 14) under same PCR condition, and the nucleotide sequence of 3'-terminal site of CJ7 promoter was obtained by PCR using the genomic DNA from ATCC 13032 strains as a template and primers (SEQ ID Nos. 15 and 16) under same PCR condition.

TABLE 4

Primers for substitution of argCJBD gene promoter

| Name | SEQ ID NO. | Sequence (5'-3') |
|---|---|---|
| argC-L-5-BamHI | 11 | CGGGATCCGCAACGCTTGCGGTGAGAGA |
| arC-L-3-EcoRI | 12 | CCGGAATTCCTGGAAGTGGTCGAAGAAGA |
| CJ7-5-EcoRI | 13 | CCGGAATTCGCCGGCATAGCCTACCGATG |
| CJ7-3-XbaI | 14 | TGCTCTAGAGATATCAGTGTTTCCTTTCG |
| artC-R-5-XbaI | 15 | TGCTCTAGAATGATAATGCATAACGTGTA |
| argC-R-3-SalI | 16 | ACGCGTCGACGCTTTCCGGAGGTGTTGTAC |

The above-prepared 5'-terminal site fragment of promoter (argC-L) was digested with BamHI and EcoRI, the CJ7 promoter region fragment was digested with EcoRI and XbaI, and the 3'-terminal site fragment of promoter (argC-R) was digested with XbaI and SalI. then each of the cleaved PCR products was cloned into the pDZ vector which was also digested with BamHI and SalI, thereby producing an expression vector pDZ-CJ7(arg) in which the promoter of argCJBD was substituted with CJ7 promoter.

The above-prepared expression vector pDZ-CJ7(arg) was transformed into ATCC 13032 ΔargF ΔNCgl1221 strain and KCCM-10785P ΔargF ΔNCgl1122I strain through electroporation. Then, the transformants were cultured with shaking in CM medium (30° C., 8 hours), and the cell culture was serially diluted from $10^{-4}$ to $10^{-10}$. Then, the diluted samples were placed and cultured on BHIS plate containing 25 μg/ml kanamycin and X-gal, letting the colonies to grow.

The white colonies which appear at low frequency were isolated from most of the blue colonies, thereby selecting only the strain where the arg promoter was successfully substituted with CJ7 promoter through double crossover.

Successful substitution of argCJBD promoter in chromosome by the introduced expression vector pDZ-CJ7(arg) was confirmed by performing PCR using the genomic DNA from the above-selected strains as a template and primers (SEQ ID Nos. 13 and 16) (28 cycles of denaturation for 30 seconds at 94° C., annealing for 30 seconds at 55° C., and extension for 60 seconds at 72° C.). Finally, the confirmed strains were named as ATCC 13032 ΔargF ΔNCgl1221 P(CJ7)-argCJBD and KCCM-10785P ΔargF ΔNCgl1221 P(CJ7)-argCJBD accordingly.

EXAMPLE 4

Improvement of Ornithine Productivity by Deletion of argF and NCgl1221 Genes and Enhancement of argCJBD Expression Level

EXAMPLE 4-1

Ornithine Productivity of ATCC 13032 *Corynebacterium Glutamicum*-cerived Strain In order to examine whether ornithine productivity is affected by deletion of argF and NCgl1221 genes and enhancement of argCJBD expression level in the ATCC 13032 *Corynebacterium glutamicum*-derived strains, the ornithine-producing ability between the strains prepared in Examples 2 and 3 was compared.

In detail, each of the strains prepared in Examples 2 and 3 (ATCC 13032 ΔargF ΔNCgl1221, ATTC 13032 ΔargF ΔNCGl1221/pHC139T-argCJBD(Cgl), ATTC 13032 ΔargF ΔNCgl1221 P(CJ7)-argCNBD) was spread on a CMA plate containing 1 mM arginine, and cultured at 37° C. for 24 hours. Each of the strains cultured was inoculated in 25 ml of titration medium (2% (w/v) glucose, 1% (w/v) polypeptone, 0.5% (w/v) yeast extract, 0.5% (w/v) $(NH_4)_2SO_4$, 0.15% (w/v) urea, 0.4% (w/v) $KH_2PO_4$, 0.8% (w/v) $K_2HPO_4$, 0.05% (w/v) $MgSO_4$, 100 μg/l biotin and 1 mg/l thiamine) containing 1 mM arginine, and then cultured with shaking at 30° C. and 200 rpm for 48 hours and the concentration of ornithine produced in the each culture was determined and compared to each other (Table 5). At this time, strain ATCC13032 with no genomic modification was used as a control group.

TABLE 5

Comparison of ornithine productivity in ATCC 13032-derived strains

| Strain | Ornithine content (g/l) |
| --- | --- |
| ATCC 13032 | 0.0 |
| ATCC 13032 ΔargF ΔNCgl1221 | 6.0 |
| ATCC 13032 ΔargF ΔNCgl1221/pHC139T-argCJBD(Cgl) | 6.4 |
| ATCC 13032 ΔargF ΔNCgl1221 P(CJ7)-argCJBD | 7.7 |

As shown in Table 5, the argF and NCgl1221-deleted strain produced 6.0 g/l of ornithine, which was not produced by the wild-type strain. With respect to the increase of argCJBD gene expression level, when the argCJBD gene was introduced in the form of vector, the concentration of the produced ornithine was 6.4 g/l, and when the argCJBD promoter on the chromosome was replaced by CJ7, the concentration of the produced ornithine was slightly increased to 7.7 g/l.

EXAMPLE 4-2

Ornithine Productivity of Glutamate-producing *Corynebacterium Glutamicum* KCCM-10785P-derived Strain In order to examine whether ornithine productivity is affected by deletion of argF and NCgl1221 genes and enhancement of argCJBD expression level in the strain *Corynebacterium glutamicum* strain KCCM-10785P overproducing glutamate, precursor of ornithine, the ornithine-producing ability between the strains prepared in Examples 2 and 3 was compared.

In detail, each of the strains prepared in Examples 2 and 3 (KCCM-10785P ΔargF ΔNCgl1221, KCCM-10785P ΔargF ΔNCgl1221/pHC139T-argCJBD(Cgl), KCCM-10785P ΔargF ΔNCgl1221 P(CJ7)-argCJBD) was inoculated in the same manner as in Example 4-1, and then cultured with shaking at 30° C. and 200 rpm for 48 hours, and the concentration of ornithine produced in each culture was determined and compared to each other (Table 6). At this time, a strain KCCM-10785P with no genetic modification was used as a control group.

TABLE 6

Comparison of ornithine productivity in KCCM-10785P-derived strains

| strain | Glutamate content (g/l) | Ornithine content (g/l) |
| --- | --- | --- |
| KCCM-10785P | 15.5 | 0.0 |
| KCCM-10785P ΔargF ΔNCgl1221 | 5.2 | 7.6 |
| KCCM-10785P ΔargF ΔNCgl1221/phC139T-argCJBD(Cgl) | 4.8 | 7.9 |
| KCCM-10785P ΔargF ΔNCgl1221 P(CJ7)-argCJBD | 2.0 | 9.0 |

As shown in Table 6, argF and NCgl1221 deletions in the glutamate-overproducing strain showed 7.6 g/l ornithine production, which was not produced by the wild-type strain. With respect to the increase of argCJBD gene expression level, when the argCJBD gene was introduced in the form of vector, the concentration of the produced ornithine was 7.9 g/l, and when the argCJBD promoter on the chromosome was replaced by CJ7, the concentration of the produced ornithine was slightly increased to 9.0 g/l.

Accordingly, it can be seen that ornithine production can be increased through enhancement of the synthetic pathway of ornithine by increasing the argCJBD gene expression level.

Therefore, the present inventor designated the strain having the most excellent ornithine productivity prepared in Example 3-2 as "CC01-0061 (ATCC 13032 ΔargF ΔNCgl1221 P(CJ7)-argCJBD)", and deposited it under the Budapest Treaty to the Korean Culture Center of Microorganisms whose address is Hongje-1-dong, Seodaemun-gu, Seoul on Nov. 24, 2010, with the Accession No. KCCM11137P.

It will be apparent to those skilled in the art that various modifications and changes may be made without departing from the scope and spirit of the invention. Therefore, it should be understood that the above embodiments are not limitative, but illustrative in all aspects. Therefore all changes and modifications that fall within metes and bounds of the claims, or equivalents of such metes and bounds are therefore intended to be embraced by the claims.

The invention claimed is:

1. A microorganism belonging to *Corynebacterium glutamicum* having an ornithine-producing ability, wherein the activities of ornithine carbamoyltransferase and a protein involved in glutamate export are modified to be attenuated, compared to their endogenous activities;
wherein the protein involved in glutamate export has an amino acid sequence of SEQ ID NO: 20, or an amino acid sequence having 70% or more homology with SEQ ID NO: 20.

2. The microorganism according to claim 1, wherein the ornithine carbamoyltransferase has an amino acid sequence of SEQ ID NO: 18, or an amino acid sequence having 70% or more homology with the sequence.

3. The microorganism according to claim 1, wherein the activity of the ornithine carbamoyltransferase and the protein involved in glutamate export is attenuated by a method selected from the group consisting of (1) a partial or full deletion of a gene coding for the protein, (2) modification of an expression regulatory sequence for suppressing the gene expression, (3) modification of the gene sequence on chromosome for diminishing the protein activity, and (4) a combination thereof.

4. The microorganism according to claim 1, wherein activities of acetyl gamma glutamyl phosphate reductase (ArgC), acetylglutamate synthase or ornithine acetyltransferase (ArgJ), acetylglutamate kinase (ArgB) and acetylornithine aminotransferase (ArgD) are further enhanced, compared to their endogenous activities.

5. The microorganism according to claim 4, wherein each of ArgC, ArgJ, ArgB, and ArgD has an amino acid sequence of SEQ ID NOs: 23, 25, 27, and 29, or an amino acid sequence having 70% or more homology with the sequence.

6. The microorganism according to claim 4, wherein the activity of proteins is enhanced by a method selected from the group consisting of (1) increase of the copy number of a polynucleotide coding for the protein, (2) modification of an expression regulatory sequence for increasing the polynucleotide expression, (3) modification of the polynucleotide sequence on a chromosome for enhancing an activity of the enzyme, and (4) a combination thereof.

7. The microorganism according to claim 1, wherein the microorganism is *Corynebacterium glutamicum*.

8. A method for producing ornithine, comprising the steps of:
(i) culturing the microorganism according to claim 1; and
(ii) recovering ornithine from the cultured microorganism or the culture.

* * * * *

SEQUENCE LISTING

<160> NUMBER OF SEQ ID NOS: 29

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
cgggatcctg gccgtaccgg cgatttct                                    28

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
cgcgtcgaca agtttgagtc ctttatgcg                                   29

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
cgcgtcgacg acatgtccct tggctcaac                               29

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
tgctctagaa gtaattcacc tagttctttta cc                          32

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
acgcgtcgac ccactcggcg cttgataata c                            31

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
acgcgtcgac ccactcggcg cttgataata c                            31

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
acgcgtcgac ctggaacaag aactctccag c                            31

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ctagtctaga ggttggtgct tccactgctg                              30

<210> SEQ ID NO 9
<211> LENGTH: 30
<212> TYPE: DNA
<213> ORGANISM: Artificial Sequence
<220> FEATURE:

<223> OTHER INFORMATION: primer

<400> SEQUENCE: 9
cggggtaccc tcctccagca gctctagctc                                              30

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
tgctctagaa agtttgagtc ctttatgcg                                               29

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
cgggatccgc aacgcttgcg gtgagaga                                                28

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
ccggaattcc tggaagtggt cgaagaaga                                               29

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
ccggaattcg ccggcatagc ctaccgatg                                               29

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
tgctctagag atatcagtgt ttcctttcg                                               29

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
tgctctagaa tgataatgca taacgtgta                                               29

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16

```
acgcgtcgac gctttccgga ggtgttgtac                                30
```

<210> SEQ ID NO 17
<211> LENGTH: 960
<212> TYPE: DNA
<213> ORGANISM: Corynebacterium glutamicum

<400> SEQUENCE: 17

```
atgacttcac aaccacaggt tcgccatttt ctggctgatg atgatctcac ccctgcagag    60
caggcagagg ttttgaccct agccgcaaag ctcaaggcag cgccgttttc ggagcgtcca   120
ctcgagggac aaagtccgt tgcagttctt tttgataaga cttcaactcg tactcgcttc   180
tccttcgacg cgggcatcgc tcatttgggt ggacacgcca tcgtcgtgga ttccggtagc   240
tcacagatgg gtaagggcga gtccctgcag gacaccgcag ctgtattgtc ccgctacgtg   300
gaagcaattg tgtggcgcac ctacgcacac agcaatttcc acgccatggc ggagacgtcc   360
actgtgccgc tggtgaactc cttgtccgat gatctgcacc catgccagat tctggctgat   420
ctgcagacta tcgtggaaaa cctcagccct gaagaaggcc agcaggcct taagggtaag    480
aaggctgtgt acctgggcga tggcgacaac aacatggcca actcctacat gattggcttt   540
gccaccgcgg gcatggatat ttccatcatc gctcctgaag ggttccagcc tcgtgcggaa   600
ttcgtggagc gcgcggaaaa gcgtggccag gaaaccggcg cgaaggttgt tgtcaccgac   660
agcctcgacg aggttgccgg cgccgatgtt gtcatcaccg atacctgggt atccatgggt   720
atggaaaacg acggcatcga tgcaccaca cctttcgttc cttaccaggt caacgatgag    780
gtcatggcga aagctaacga cggcgccatc ttcctgcact gccttcctgc ctaccgtggc   840
aaagaagtgg cagcctccgt gattgatgga ccagcgtcca agttttcga tgaagcagaa    900
aaccgcctcc acgctcagaa agcactgctg gtgtggctgc tggccaacca gccgaggtaa    960
```

<210> SEQ ID NO 18
<211> LENGTH: 319
<212> TYPE: PRT
<213> ORGANISM: Corynebacterium glutamicum

<400> SEQUENCE: 18

```
Met Thr Ser Gln Pro Gln Val Arg His Phe Leu Ala Asp Asp Asp Leu
1               5                  10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
    50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110
```

```
Phe His Ala Met Ala Glu Thr Ser Thr Val Pro Leu Val Asn Ser Leu
            115                 120                 125

Ser Asp Asp Leu His Pro Cys Gln Ile Leu Ala Asp Leu Gln Thr Ile
130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Arg Ala Glu Lys Arg
        195                 200                 205

Gly Gln Glu Thr Gly Ala Lys Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Asn Arg Leu His
    290                 295                 300

Ala Gln Lys Ala Leu Leu Val Trp Leu Leu Ala Asn Gln Pro Arg
305                 310                 315
```

<210> SEQ ID NO 19
<211> LENGTH: 1602
<212> TYPE: DNA
<213> ORGANISM: Corynebacterium glutamicum

<400> SEQUENCE: 19

```
atgattttag cgtacccat tcaatatttg ctctattcat tgtggaattg gattgtcgat      60
accggttttg atgtagcaat tatcctggtc ttggcgtttt tgattccacg tatcggccga     120
ctggccatgc gtattatcaa cgccgagtg gagtctgcag ccgatgcgga caccactaag     180
aaccagctcg cgttcgccgg cgttggcgtt tatatcgcgc aaattgtggc gttttcatg      240
cttgccgtct ccgcgatgca ggcttttggt ttctctctcg cgggcgctgc gattccggca     300
accattgcgt cagctgccat tggccttggt gcgcagtcga ttgttgcgga cttcttggcc     360
ggattttca tcctgacgga aaagcaattc ggcgtgggtg actgggtgcg ttttgagggc     420
aacggcatcg ttgtcgaagg caccgtcatt gagatcacca tgcgcgcgac caaaattcgc     480
acgattgcac aagagaccgt gatcatcccc aactccacgg cgaaagtgtg catcaacaat     540
tctaataact ggtcgcgtgc ggttgtcgtt attccgatcc ccatgttggg ttctgaaaac     600
atcacagatg tcatcgcgcg ctctgaagct gcgactcgtc gcgcacttgg ccaggagaaa     660
atcgcaccgg aaatcctcgg tgaactcgat gtgcacccag ccacggaagt cacgccgcca     720
acggtggtcg gcatgccgtg gatggtcacc atgcgtttcc tcgtgcaagt caccgccggc     780
aatcaatggc tggtcgaacg cgccatccgc acagaaatca tcagcgaatt ctgggaagaa     840
tacggcagcg caaccactac atcgggaacc ctcattgatt ccttacacgt tgagcatgaa     900
gagccaaaga cctcgcttat cgacgcctcc ccccaggctc ttaaggaacc gaagccggag     960
```

```
gctgcggcga cggttgcatc gctagctgca tcctctaacg acgatgcaga caatgcagac   1020
gcctcggtga tcaatgcagg caatccagag aaggaacttg attccgatgt gctggaacaa   1080
gaactctcca gcgaagaacc ggaagaaaca gcaaaaccag atcactctct ccgaggcttc   1140
ttccgcactg attactaccc aaatcggtgg cagaagatcc tgtcgtttgg cggacgtgtc   1200
cgcatgagca cgtccctgtt gttgggtgcg ctgctcttgc tgtcactatt taaggtcatg   1260
actgtggaac caagtgagaa ttggcaaaac tccagtggat ggctgtcacc aagcactgcc   1320
acctcaactg cggtgaccac ctccgaaact tccgcgccag taagcacgcc ttcgatgaca   1380
gtgcccacta cggtggagga gaccccaacg atggaatcta acgtcgaaac gcagcaggaa   1440
acctcaaccc ctgcaaccgc aacgccccag cgagccgaca ccatcgaacc gaccgaggaa   1500
gccacgtcgc aggaggaaac gactgcgtcg cagacgcagt ctccagcagt ggaagcacca   1560
accgcggtcc aagagacagt tgcgccgacg tccaccccctt ag                     1602
```

<210> SEQ ID NO 20
<211> LENGTH: 533
<212> TYPE: PRT
<213> ORGANISM: Corynebacterium glutamicum

<400> SEQUENCE: 20

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255
```

Val Thr Ala Gly Asn Gln Trp Leu Val Glu Arg Ala Ile Arg Thr Glu
            260                 265                 270

Ile Ile Ser Glu Phe Trp Glu Tyr Gly Ser Ala Thr Thr Thr Ser
            275                 280                 285

Gly Thr Leu Ile Asp Ser Leu His Val Glu His Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
            435                 440                 445

Glu Thr Ser Ala Pro Val Ser Thr Pro Ser Met Thr Val Pro Thr Thr
450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
                500                 505                 510

Gln Ser Pro Ala Val Glu Ala Pro Thr Ala Val Gln Glu Thr Val Ala
            515                 520                 525

Pro Thr Ser Thr Pro
        530

<210> SEQ ID NO 21
<211> LENGTH: 4733
<212> TYPE: DNA
<213> ORGANISM: Corynebacterium glutamicum

<400> SEQUENCE: 21
ggctacttcc gaggaatctt ccgcagttga agagccagca gtggaagctc ctgtggaaga      60
ggctccagtc gaggcacctg ttgagcaggc acctgtcgtg gagcaagctc cagttgagca     120
ggctccggca ccggttcagg aagcacctgc accagtcgag caggctccag ctccagttca     180
ggaagcacct gcagctgacg cgccacctgc acttccaggt ggtggcggcg acacgctgg      240 ctactaaaaa ttcatgcttt tacccacttg cagttttagc tgtaggtggg ttttttgcatg    300 tctaacccgt cttttatgca caccccccgca atgaatcaaa aatttatgca tgaataatttt   360 gcatgatcat gcataacgtg tatggtgtaa ctatgacaat caaggttgca atcgcaggag     420
ccagtggata tgccggcgga gaaatccttc gtctcctttt aggccatcca gcttatgcat     480
ctggtgaact agaaatcgga gcactcaccg cggcatcaac cgcaggcagc acgctcggtg     540

```
aattgatgcc acacattccg cagttggcgg atcgtgttat tcaagacacc acagctgaaa      600
ctctagccgg tcatgatgtc gtatttctag gacttccaca cggattctct gcagaaattg      660
cacttcagct cggaccagat gtcacagtga ttgactgtgc agctgacttt cgtctgcaaa      720
atgctgcaga ttgggagaag ttctacggct cagagcacca gggaacatgg ccttatggca      780
ttccagaaat gccaggacac cgcgaggctc ttcgtggtgc taagcgtgta gcagtgccag      840
gatgtttccc aaccggtgca accttggctc ttcttcctgc ggttcaagcg ggacttatcg      900
agccagatgt ttccgtagtg tccatcaccg gcgtatcagg tgcaggtaag aaagcatctg      960
ttgcactact tggctcggaa accatggggtt cactcaaggc gtacaacacc tccggaaagc     1020
accgccacac cccggaaatt gcccagaacc tcggcgaagt cagcgacaag ccagtcaagg     1080
tgagcttcac cccagtgctt gcaccgttac ctcgcgaat tctcaccact gcaaccgcac      1140 cttttgaaaga aggcgttacc gcagaacagg ctcgcgcagt atatgaagag ttctatgcac     1200
aggaaacctt cgtgcatgtt cttccagaag gtgcacagcc acaaacccaa gcagttcttg     1260
gctccaacat gtgccacgtg caggtagaaa ttgatgagga agcaggcaaa gtccttgtta     1320
cctccgcaat cgataacctc accaagggaa ctgccggcgc cgctgttcag tgcatgaact     1380
taagcgttgg ttttgatgag gcagcaggcc tgccacaggt cggcgtcgca ccttaaatgg     1440
cagaaaaagg cattaccgcg ccgaaaggct tcgttgcttc tgcaacgacc gcgggtatta     1500
aagcttctgg caatcctgac atggcgttgg tggttaacca gggtccagag ttttccgcag     1560
cggccgtgtt tacacgtaac cgagttttcg cagcgcctgt gaaggtgagc cgagagaacg     1620
ttgctgatgg ccagatcagg gctgttttgt acaacgctgg taatgctaat gcgtgtaatg     1680
gtctgcaggg tgagaaggat gctcgtgagt ctgtttctca tctagctcaa aatttgggct     1740
tggaggattc cgatattggt gtgtgttcca ctggtcttat tggtgagttg cttccgatgg     1800
ataagctcaa tgcaggtatt gatcagctga ccgctgaggg cgctttgggt gacaatggtg     1860
cagctgctgc caaggcgatc atgaccactg acacggtgga taaggaaacc gtcgtgtttg     1920
ctgatggttg gactgtcggc ggaatgggca agggcgtggg catgatggcg ccgtctcttg     1980
ccaccatgct ggtctgcttg accactgatg catccgttac tcaggaaatg gctcagatcg     2040
cgctggctaa tgctacggcc gttacgtttg acaccctgga tattgatgga tcaacctcca     2100
ccaatgacac cgtgttcctg ctggcatctg gcgctagcgg aatcaccccca actcaggatg     2160 aactcaacga tgcggtgtac gcagcttgtt ctgatatcgc agcgaagctt caggctgatg     2220
cagagggtgt gaccaagcgc gttgctgtga cagtggtggg aaccaccaac aacgagcagg     2280
cgattaatgc ggctcgcact gttgctcgtg acaatttgtt caagtgcgca atgtttggat     2340
ctgatccaaa ctggggtcgc gtgttggctg cagtcggcat ggctgatgct gatatggaac     2400
cagagaagat ttctgtgttc ttcaatggtc aagcagtatg ccttgattcc actggcgctc     2460
ctggtgctcg tgaggtggat ctttccggcg ctgacattga tgtccgaatt gatttgggca     2520
ccagtgggga aggccaggca acagttcgaa ccactgacct gagcttctcc tacgtggaga     2580
tcaactccgc gtacagctct taaatgaatg acttgatcaa agatttaggc tctgaggtgc     2640
gcgcaaatgt cctcgctgag gcgttgccat ggttgcagca cttccgcgac aagattgttg     2700
tcgtgaaata tggcggaaac gccatggtgg atgatgatct caaggctgct tttgctgccg     2760
acatggtctt cttgcgcacc gtgggcgcaa accagtgggg ggtgcacggt ggtggacctc     2820
agatttctga gatgctaaac cgtgtgggtc tccagggcga gttcaagggt ggtttccgtg     2880
```

-continued

| | |
|---|---|
| tgaccactcc tgaggtcatg acattgtgc gcatggtgct ctttggtcag gtcggtcgcg | 2940 |
| atttagttgg tttgatcaac tctcatggcc cttacgctgt gggaacctcc ggtgaggatg | 3000 |
| ccggcctgtt taccgcgcag aagcgcatgg tcaacatcga tggcgtaccc actgatattg | 3060 |
| gtttggtcgg agacatcatt aatgtcgatg cctcttcctt gatggatatc atcgaggccg | 3120 |
| gtcgcattcc tgtggtctct acgattgctc caggcgaaga cggccagatt tacaacatta | 3180 |
| acgccgatac cgcagcaggt gctttggctg cagcgattgg tgcagaacgc ctgctggttc | 3240 |
| tcaccaatgt ggaaggtctg tacaccgatt ggcctgataa gagctcactg gtgtccaaga | 3300 |
| tcaaggccac cgagctggag ccattcttc cgggacttga ttccggcatg attccaaaga | 3360 |
| tggagtcttg cttgaacgcg gtgcgtgggg gagtaagcgc tgctcatgtc attgacggcc | 3420 |
| gcatcgcgca ctcggtgttg ctggagcttt tgaccatggg tggaattggc acgatggtgc | 3480 |
| tgccggatgt ttttgatcgg gagaattatc ctgaaggcac cgttttttaga aaagacgaca | 3540 |
| aggatgggga actgtaaatg agcacgctgg aaacttggcc acaggtcatt attaatacgt | 3600 |
| acggcacccc accagttgag ctggtgtccg gcaagggcgc aaccgtcact gatgaccagg | 3660 |
| gcaatgtcta catcgacttg ctcgcgggca tcgcagtcaa cgcgttgggc cacgcccacc | 3720 |
| cggcgatcat cgaggcggtc accaaccaga tcggccaact tggtcacgtc tcaaacttgt | 3780 |
| tcgcatccag gcccgtcgtc gaggtcgccg aggagctcat caagcgtttt tcgcttgacg | 3840 |
| acgccaccct cgccgcgcaa acccgggttt tcttctgcaa ctcgggcgcc gaagcaaacg | 3900 |
| aggctgcttt caagattgca cgcttgactg gtcgttcccg gattctggct gcagttcatg | 3960 |
| gtttccacgg ccgcaccatg ggttccctcg cgctgactgg ccagccagac aagcgtgaag | 4020 |
| cgttcctgcc aatgccaagc ggtgtggagt ctacccctta cggcgacacc gattacttgc | 4080 |
| gcaaaatggt agaaaccaac ccaacggatg tggctgctat cttcctcgag ccaatccagg | 4140 |
| gtgaaacggg cgttgttcca gcacctgaag gattcctcaa ggcagtgcgc gagctgtgcg | 4200 |
| atgagtacgc catcttgatg atcaccgatg aagtccagac tggcgttggc cgtaccggcg | 4260 |
| atttctttgc acatcagcac gatggcgttg ttcccgatgt ggtgaccatg gccaagggac | 4320 |
| ttggcggcgg tcttcccatc ggtgcttgtt tggccactgg ccgtgcagct gaattgatga | 4380 |
| ccccaggcaa gcacggcacc actttcggtg caacccagt tgcttgtgca gctgccaagg | 4440 |
| cagtgctgtc tgttgtcgat gacgctttct gcgcagaagt tgcccgcaag ggcgagctgt | 4500 |
| tcaaggaact tcttgccaag gttgacggcg ttgtagacgt ccgtggcagg ggcttgatgt | 4560 |
| tgggcgtggt gctggagcgc gacgtcgcaa agcaagctgt tcttgatggt tttaagcacg | 4620 |
| gcgttatttt gaatgcaccg gcggacaaca ttatccgttt gaccccgccg ctggtgatca | 4680 |
| ccgacgaaga aatcgcagac gcagtcaagg ctattgccga gacaatcgca taa | 4733 |

<210> SEQ ID NO 22
<211> LENGTH: 1074
<212> TYPE: DNA
<213> ORGANISM: Corynebacterium glutamicum

<400> SEQUENCE: 22

| | |
|---|---|
| atgatcatgc ataacgtgta tggtgtaact atgacaatca aggttgcaat cgcaggagcc | 60 |
| agtggatatg ccggcggaga aatccttcgt ctccttttag gccatccagc ttatgcatct | 120 |
| ggtgaactag aaatcggagc actcaccgcg gcatcaaccg caggcagcac gctcggtgaa | 180 |
| ttgatgccac acattccgca gttggcggat cgtgttattc aagacaccac agctgaaact | 240 |
| ctagccggtc atgatgtcgt atttctagga cttccacacg gattctctgc agaaattgca | 300 |

```
cttcagctcg gaccagatgt cacagtgatt gactgtgcag ctgactttcg tctgcaaaat    360
gctgcagatt gggagaagtt ctacggctca gagcaccagg gaacatggcc ttatggcatt    420
ccagaaatgc caggacaccg cgaggctctt cgtggtgcta agcgtgtagc agtgccagga    480
tgtttcccaa ccggtgcaac cttggctctt cttcctgcgg ttcaagcggg acttatcgag    540
ccagatgttt ccgtagtgtc catcaccggc gtatcaggtg caggtaagaa agcatctgtt    600
gcactacttg gctcggaaac catgggttca ctcaaggcgt acaacacctc cggaaagcac    660
cgccacaccc cggaaattgc ccagaacctc ggcgaagtca gcgacaagcc agtcaaggtg    720
agcttcaccc cagtgcttgc accgttacct cgcggaattc tcaccactgc aaccgcacct    780
ttgaaagaag gcgttaccgc agaacaggct cgcgcagtat atgaagagtt ctatgcacag    840
gaaaccttcg tgcatgttct tccagaaggt gcacagccac aaacccaagc agttcttggc    900
tccaacatgt gccacgtgca ggtagaaatt gatgaggaag caggcaaagt ccttgttacc    960
tccgcaatcg ataacctcac caagggaact gccggcgccg ctgttcagtg catgaactta   1020
agcgttggtt ttgatgaggc agcaggcctg ccacaggtcg gcgtcgcacc ttaa         1074
```

<210> SEQ ID NO 23
<211> LENGTH: 357
<212> TYPE: PRT
<213> ORGANISM: Corynebacterium glutamicum

<400> SEQUENCE: 23

```
Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
    50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
    130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
    210                 215                 220

Glu Ile Ala Gln Asn Leu Gly Glu Val Ser Asp Lys Pro Val Lys Val
225                 230                 235                 240
```

```
Ser Phe Thr Pro Val Leu Ala Pro Leu Pro Arg Gly Ile Leu Thr Thr
            245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
        275                 280                 285

Glu Gly Ala Gln Pro Gln Thr Gln Ala Val Leu Gly Ser Asn Met Cys
        290                 295                 300

His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
            340                 345                 350

Val Gly Val Ala Pro
        355
```

<210> SEQ ID NO 24
<211> LENGTH: 1167
<212> TYPE: DNA
<213> ORGANISM: Corynebacterium glutamicum

<400> SEQUENCE: 24

```
atggcagaaa aaggcattac cgcgccgaaa ggcttcgttg cttctgcaac gaccgcgggt      60
attaaagctt ctggcaatcc tgacatggcg ttggtggtta accagggtcc agagttttcc     120
gcagcggccg tgtttacacg taaccgagtt ttcgcagcgc ctgtgaaggt gagccgagag     180
aacgttgctg atggccagat cagggctgtt ttgtacaacg ctggtaatgc taatgcgtgt     240
aatggtctgc agggtgagaa ggatgctcgt gagtctgttt ctcatctagc tcaaaatttg     300
ggcttggagg attccgatat tggtgtgtgt tccactggtc ttattggtga gttgcttccg     360
atggataagc tcaatgcagg tattgatcag ctgaccgctg agggcgcttt gggtgacaat     420
ggtgcagctg ctgccaaggc gatcatgacc actgacacgg tggataagga accgtcgtg      480
tttgctgatg gttggactgt cggcggaatg ggcaagggcg tgggcatgat ggcgccgtct     540
cttgccacca tgctggtctg cttgaccact gatgcatccg ttactcagga atggctcag      600
atcgcgctgg ctaatgctac ggccgttacg tttgacaccc tggatattga tggatcaacc     660
tccaccaatg acaccgtgtt cctgctggca tctggcgcta gcggaatcac cccaactcag     720
gatgaactca cgatgcggt gtacgcagct tgttctgata tcgcagcgaa gcttcaggct     780
gatgcagagg gtgtgaccaa gcgcgttgct gtgacagtgg tgggaaccac caacaacgag     840
caggcgatta atgcggctcg cactgttgct cgtgacaatt tgttcaagtg cgcaatgttt     900
ggatctgatc caaactgggg tcgcgtgttg ctgcagtcg gcatggctga tgctgatatg     960
gaaccagaga gatttctgt gttcttcaat ggtcaagcag tatgccttga ttccactggc    1020
gctcctggtg ctcgtgaggt ggatctttcc ggcgctgaca ttgatgtccg aattgatttg    1080
ggcaccagtg gggaaggcca ggcaacagtt cgaaccactg acctgagctt ctcctacgtg    1140
gagatcaact ccgcgtacag ctcttaa                                        1167
```

<210> SEQ ID NO 25
<211> LENGTH: 388
<212> TYPE: PRT
<213> ORGANISM: Corynebacterium glutamicum

<400> SEQUENCE: 25

```
Met Ala Glu Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Val Phe Thr Arg Asn
        35                  40                  45

Arg Val Phe Ala Ala Pro Val Lys Val Ser Arg Glu Asn Val Ala Asp
    50                  55                  60

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385
```

<210> SEQ ID NO 26

<211> LENGTH: 954
<212> TYPE: DNA
<213> ORGANISM: Corynebacterium glutamicum

<400> SEQUENCE: 26

```
atgaatgact tgatcaaaga tttaggctct gaggtgcgcg caaatgtcct cgctgaggcg      60
ttgccatggt tgcagcactt ccgcgacaag attgttgtcg tgaaatatgg cggaaacgcc     120
atggtggatg atgatctcaa ggctgctttt gctgccgaca tggtcttctt gcgcaccgtg     180
ggcgcaaaac cagtggtggt gcacggtggt ggacctcaga tttctgagat gctaaaccgt     240
gtgggtctcc agggcgagtt caagggtggt ttccgtgtga ccactcctga ggtcatggac     300
attgtgcgca tggtgctctt tggtcaggtc ggtcgcgatt tagttggttt gatcaactct     360
catggccctt acgctgtggg aacctccggt gaggatgccg gcctgtttac cgcgcagaag     420
cgcatggtca acatcgatgg cgtacccact gatattggtt tggtcggaga catcattaat     480
gtcgatgcct cttccttgat ggatatcatc gaggccggtc gcattcctgt ggtctctacg     540
attgctccag gcgaagacgg ccagatttac aacattaacg ccgataccgc agcaggtgct     600
ttggctgcag cgattggtgc agaacgcctg ctggttctca ccaatgtgga aggtctgtac     660
accgattggc ctgataagag ctcactggtg tccaagatca aggccaccga gctggaggcc     720
attcttccgg gacttgattc cggcatgatt ccaaagatgg agtcttgctt gaacgcggtg     780
cgtggggag taagcgctgc tcatgtcatt gacggccgca tcgcgcactc ggtgttgctg     840
gagcttttga ccatgggtgg aattggcacg atggtgctgc cggatgtttt tgatcgggag     900
aattatcctg aaggcaccgt ttttagaaaa gacgacaagg atggggaact gtaa           954
```

<210> SEQ ID NO 27
<211> LENGTH: 317
<212> TYPE: PRT
<213> ORGANISM: Corynebacterium glutamicum

<400> SEQUENCE: 27

```
Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Asp Leu Lys Ala
        35                  40                  45

Ala Phe Ala Ala Asp Met Val Phe Leu Arg Thr Val Gly Ala Lys Pro
    50                  55                  60

Val Val Val His Gly Gly Gly Pro Gln Ile Ser Glu Met Leu Asn Arg
65                  70                  75                  80

Val Gly Leu Gln Gly Glu Phe Lys Gly Gly Phe Arg Val Thr Thr Pro
            85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
        115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175
```

Val Val Ser Thr Ile Ala Pro Gly Glu Asp Gly Gln Ile Tyr Asn Ile
              180                 185                 190

Asn Ala Asp Thr Ala Ala Gly Ala Leu Ala Ala Ala Ile Gly Ala Glu
            195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
                260                 265                 270

Arg Ile Ala His Ser Val Leu Leu Glu Leu Leu Thr Met Gly Gly Ile
            275                 280                 285

Gly Thr Met Val Leu Pro Asp Val Phe Asp Arg Glu Asn Tyr Pro Glu
    290                 295                 300

Gly Thr Val Phe Arg Lys Asp Lys Asp Gly Glu Leu
305                 310                 315

<210> SEQ ID NO 28
<211> LENGTH: 1176
<212> TYPE: DNA
<213> ORGANISM: Corynebacterium glutamicum

<400> SEQUENCE: 28

```
atgagcacgc tggaaacttg gccacaggtc attattaata cgtacggcac cccaccagtt      60
gagctggtgt ccggcaaggg cgcaaccgtc actgatgacc agggcaatgt ctacatcgac     120
ttgctcgcgg gcatcgcagt caacgcgttg ggccacgccc accggcgat catcgaggcg     180
gtcaccaacc agatcggcca acttggtcac gtctcaaact tgttcgcatc caggcccgtc     240
gtcgaggtcg ccgaggagct catcaagcgt ttttcgcttg acgacgccac cctcgccgcg     300
caaacccggg ttttcttctg caactcgggc gccgaagcaa acgaggctgc tttcaagatt     360
gcacgcttga ctggtcgttc ccggattctg gctgcagttc atggtttcca cggccgcacc     420
atgggttccc tcgcgctgac tggccagcca gacaagcgtg aagcgttcct gccaatgcca     480
agcggtgtgg agttctaccc ttacggcgac accgattact gcgcaaaat ggtagaaacc     540
aacccaacgg atgtggctgc tatcttcctc gagccaatcc agggtgaaac gggcgttgtt     600
ccagcacctg aaggattcct caaggcagtg cgcgagctgt gcgatgagta cggcatcttg     660
atgatcaccg atgaagtcca gactggcgtt ggccgtaccg cgatttctt tgcacatcag     720
cacgatggcg ttgttcccga tgtggtgacc atggccaagg acttggcgg cggtcttccc     780
atcggtgctt gtttggccac tggccgtgca gctgaattga tgaccccagg caagcacggc     840
accactttcg gtggcaaccc agttgcttgt gcagctgcca aggcagtgct gtctgttgtc     900
gatgacgctt tctgcgcaga agttgcccgc aagggcgagc tgttcaagga acttcttgcc     960
aaggttgacg gcgttgtaga cgtccgtggc aggggcttga tgttgggcgt ggtgctggag    1020
cgcgacgtcg caaagcaagc tgttcttgat ggttttaagc acggcgttat tttgaatgca    1080
ccggcggaca acattatccg tttgaccccg ccgctggtga tcaccgacga agaaatcgca    1140
gacgcagtca aggctattgc cgagacaatc gcataa                              1176
```

<210> SEQ ID NO 29
<211> LENGTH: 391
<212> TYPE: PRT

<213> ORGANISM: Corynebacterium glutamicum

<400> SEQUENCE: 29

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Asn Val Tyr Ile Asp Leu Leu Ala Gly Ile Ala Val Asn
        35                  40                  45

Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
290                 295                 300

Cys Ala Glu Val Ala Arg Lys Gly Glu Leu Phe Lys Glu Leu Leu Ala
305                 310                 315                 320

Lys Val Asp Gly Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
370                 375                 380

Ala Ile Ala Glu Thr Ile Ala
385                 390